United States Patent
Ohlsen et al.

(10) Patent No.: US 8,609,102 B2
(45) Date of Patent: Dec. 17, 2013

(54) **ANTIBODIES OR FRAGMENTS THEREOF DIRECTED AGAINST A *STAPHYLOCOCCUS AUREUS* EPITOPE OF ISAA OR ISAB**

(75) Inventors: Knut Ohlsen, Wurzburg (DE); Udo Lorenz, Wurzburg (DE)

(73) Assignee: Julius-Maximilians-Universitat, Wurzburg (DE)

( * ) Notice: Subject to any disclaimer, the term of this patent is extended or adjusted under 35 U.S.C. 154(b) by 0 days.

(21) Appl. No.: 13/320,743

(22) PCT Filed: May 18, 2010

(86) PCT No.: PCT/EP2010/056827
§ 371 (c)(1),
(2), (4) Date: Dec. 30, 2011

(87) PCT Pub. No.: WO2010/133600
PCT Pub. Date: Nov. 25, 2010

(65) Prior Publication Data
US 2012/0100151 A1    Apr. 26, 2012

Related U.S. Application Data

(60) Provisional application No. 61/179,133, filed on May 18, 2009.

(51) Int. Cl.
*A61K 39/40* (2006.01)
*C12P 21/08* (2006.01)

(52) U.S. Cl.
USPC ............... 424/165.1; 424/150.1; 530/387.3; 530/388.4

(58) Field of Classification Search
None
See application file for complete search history.

(56) References Cited

FOREIGN PATENT DOCUMENTS

DE    4238806 A1    5/1993
WO    WO03046007 A3    3/2004

OTHER PUBLICATIONS

Rudikoff et al (Proc. Natl. Acad. Sci. USA, 79(6):1979-1983, Mar. 1982).*
Colman P. M. (Research in Immunology, 145:33-36, 1994).*
Bendig M. M. (Methods: A Companion to Methods in Enzymology, 1995; 8:83-93).*
MacCallum et al (J. Mol. Biol., 262,732-745, 1996).*
Casset et al (Biochemical and Biophysical Research Communications, 307:198-205, 2003).*
Lederman et al (Molecular Immunology 28:1171-1181, 1991).*
Lorenz et al., "Immunodominant proteins in human sepsis caused by methicillin resistant *Staphylococcus aureus*," Advances in Experimental Medicine and Biology 485:273-278 (2000), XP008124405.
Lorenz et al., "Human antibody response during sepsis against targets expressed by methicillin resistant *Staphylococcus aureus*," FEMS Immunology and Medical Microbiology 29(2):145-153 (2000), XP002593023.
Ohlsen et al., "Development of antibody-based therapy targeting immunodominant antigens of *Staphylococcus aureus*," IJMM International Journal of Medical Microbiology 297(Supp 43):128 (Sep. 2007), XP008124403.
Quiel et al., "Electrical protein array chips for the detection of *Staphylococcal* virulence factors," Applied Microbiology and Biotechnology FEB 85(5):1619-1627 (201002), XP002593024.

* cited by examiner

*Primary Examiner* — Padma V Baskar
(74) *Attorney, Agent, or Firm* — Birch, Stewart, Kolasch & Birch, LLP

(57) ABSTRACT

The invention concerns antibodies or fragments thereof that are directed against a *Staphylococcus aureus* epitope.

5 Claims, 6 Drawing Sheets ated at the DSMZ under accession number DSM ACC2987 or DSM ACC2988.

ANTIBODIES OR FRAGMENTS THEREOF DIRECTED AGAINST A *STAPHYLOCOCCUS AUREUS* EPITOPE OF ISAA OR ISAB

This application is a U.S. National Phase filing under 35 U.S.C. §371 of International Application No. PCT/EP2010/056827, filed on May 18, 2010, which claims priority of U.S. Provisional Application No. 61/179,133, filed on May 18, 2009. The disclosures of International Application No. PCT/EP2010/056827 and U.S. Provisional Application No. 61/179,133 are incorporated herein by reference in their entirety.

The invention concerns antibodies or fragments thereof that are directed against a *Staphylococcus aureus* (=*S. aureus*) epitope, a kit containing these antibodies or fragments, a use of these antibodies or fragments, a hybridoma cell line which produces these antibodies and a method of treatment.

From FEMS Imunol. Med. Microbial. 2000 October; 29(2), pages 145 to 153 immunodominant structures which were expressed in vivo during sepsis caused by methicillin resistant *Staphylococcus aureus* (MRSA) are known. These structures are the 29 kDa protein IsaA and the 17 kDa protein IsaB. It is stated that these proteins may serve as potential targets for the development of antibody based therapy against MRSA.

From the abstract "Development of antibody-based therapy targeting immunodominant antigens of *Staphylococcus aureus*", Ohlsen, K. et al., page 128 of the abstract book published for the 59$^{th}$ annual conference of the Deutsche Gesellschaft für Hygiene und Mikrobiologie e.V. on September 2007 and from Lorenz, U. et al., "Therapeutische Effektivität von monoklonalen Antikörpern gegen *Staphylococcus aureus* in einem Sepsis- und Abszess-Mausmodell", Chirurgisches Forum 2008, Springer Berlin Heidelberg, 29$^{th}$ May 2008, issue 17, pp. 225-226 the application of a first murine monoclonal antibody targeting the immunodominant antigen IsaA in two animal infection models is known. The study revealed that application of anti-IsaA MAB lowers the infection burden in both infection models.

The object of the present invention is to provide novel antibodies or fragments thereof that are well suited for a treatment of infections caused by *Staphylococcus aureus* and for a detection of *S. aureus*. Furthermore, a kit containing these antibodies or fragments, a use of these antibodies or fragments, a hybridoma cell line secreting these antibodies or fragments and a method of treatment shall be provided.

According to the invention antibodies or fragments thereof are provided, wherein said antibodies or fragments are directed against a *Staphylococcus aureus* epitope that is recognized by monoclonal further antibodies which are secreted by the hybridoma cell line deposited at the "Deutsche Sammlung von Mikroorganismen and Zellkulturen GmbH, Inhoffenstr. 7B, D-38124 Braunschweig, Germany" (DSMZ) under accession number DSM ACC2987 or DSM ACC2988. The hybridoma cell line deposited at the DSMZ under accession number DSM ACC2987 is further designated as "cell line DSM ACC2987" and the hybridoma cell line deposited at the DSMZ under accession number DSM ACC2988 is further designated as "cell line DSM ACC2988". The monoclonal further antibodies which are secreted by cell lines DSM ACC2987 and DSM ACC2988 are monoclonal mouse antibodies.

The antibodies according to the invention comprise full immunoglobulin molecules, preferably IgMs, IgDs, IgEs, IgAs or IgGs, more preferably IgG1, IgG2a, IgG2b, IgG3 or IgG4, whereas the fragments comprise parts of such immunoglobulin molecules, like Fab fragments or V-, VH- or CDR-regions. Furthermore, the antibodies comprise modified and/or altered antibodies, like chimeric and humanized antibodies. The antibodies also comprise modified or altered monoclonal or polyclonal antibodies as well as recombinantly or synthetically generated or synthesized antibodies. The fragments comprise antibody fragments as well as parts thereof, like, separated light and heavy chains, Fab, Fab/c, Fv, Fab', F(ab')$_2$. The antibodies according to the invention also comprise antibody derivatives like bifunctional antibodies and antibody constructs, like single chain Fvs (scFv), bispecific scFvs or antibody-fusion proteins. All antibody derivatives exhibit the binding specificity of the antibodies they are derived from, i.e. they are directed against a *Staphylococcus aureus* epitope that is recognized by the monoclonal further antibodies secreted by the hybridoma cell lines DSM ACC2987 or DSM ACC2988.

The epitope that is recognized by the monoclonal further antibodies which are secreted by the cell line DSM ACC2987 is located on the immunodominant *S. aureus* antigen IsaA. The epitope that is recognized by the monoclonal further antibodies which are secreted by the cell line DSM ACC2988 is located on the immunodominant *S. aureus* antigen IsaB. The inventors of the present invention found that the epitopes recognized by the antibodies according to the invention are particularly exposed on *S. aureus*. Antibodies or fragments thereof that are directed against these epitopes are well suited for the detection of *S. aureus* and for the treatment of an infection with *S. aureus*. Owing to the high variability of *S. aureus* that causes different extends of expression and mutations of the antigens on different strains every antibody that recognizes an additional epitope not recognized by other antibodies is useful for the detection of *S. aureus* as well as for the treatment of a *S. aureus* infection.

The antibodies may be polyclonal or monoclonal antibodies. In particular the antibodies may be the monoclonal further antibodies, i.e. the antibodies which are secreted by the hybridoma cell line DSM ACC2987 or DSM ACC2988. These antibodies are very useful for the detection of *S. aureus* as well as for the treatment of an infection. They exhibit very high affinities and specificities. The high affinity of the antibodies which are secreted by the hybridoma cell line DSM ACC2987 to the epitope that is recognized by these antibodies is indicated by a low $K_D$ value for the binding of said antibody to said epitope. Depending on the method of determination $K_D$ values of ≤18 pM and 1.7 nM have been determined for this binding (see FIGS. 6 and 7 and corresponding text).

The monoclonal antibodies or the antibodies which are secreted by the hybridoma cell line DSM ACC2987 and/or DSM ACC2988 may be antibodies of the IgG type, in particular of the IgG1 type or the IgG2b type. The fragments may be Fab fragments, Fab/c fragments, Fv fragments, Fab' fragments or F(ab')$_2$ fragments. These fragments are particularly useful for the detection of *S. aureus* because the cell wall of *S. aureus* contains protein A which unspecifically binds immunglobulins via their Fc-parts.

The antibodies may be animal antibodies, i.e. antibodies produced in an animal, especially murine, bovine, or camel antibodies, human antibodies, antibodies produced in a plant, an egg or a fungus, in particular a *Saccharomyces*, recombinant antibodies produced in cells of a cell line, chimeric antibodies, or humanized antibodies. A humanized antibody may be a monoclonal antibody that contains the binding portion of a monoclonal mouse antibody, e.g. the monoclonal antibody secreted by the hybridoma cell line DSM ACC2987 or DSM ACC2988, and the none binding portion of a human antibody.

Each of the antibodies may have a heavy chain with a first variable region and a light chain with a second variable region, wherein the hybridoma cell line is DSM ACC2987 and wherein the first variable region comprises an amino acid sequence that is at least 90% identical, in particular at least 92.5% identical, in particular at least 95% identical, in particular at least 97.5% identical, in particular 100% identical, with sequence SEQ ID NO: 2 and wherein the second variable region comprises an amino acid sequence that is at least 90% identical, in particular at least 92.5% identical, in particular at least 95% identical, in particular at least 97.5% identical, in particular 100% identical, with sequence SEQ ID NO: 4 or wherein the hybridoma cell line is DSM ACC2988 and wherein the first variable region comprises an amino acid sequence that is at least 90% identical, in particular at least 92.5% identical, in particular at least 95% identical, in particular at least 97.5% identical, in particular 100% identical, with sequence SEQ ID NO: 6 and wherein the second variable region comprises an amino acid sequence that is at least 90% identical, in particular at least 92.5% identical, in particular at least 95% identical, in particular at least 97.5% identical, in particular 100% identical, with sequence SEQ ID NO: 8.

The first variable region and the second variable region as characterized above together form a binding site having high affinity to and specifity for the epitope.

One possible DNA sequence encoding the first variable region according to SEQ ID NO: 2 is sequence SEQ ID NO: 1. SEQ ID NO: 1 is the sequence encoding the first variable region of the antibodies secreted by cell line DSM ACC2987. The second variable region according to SEQ ID NO: 4 may be encoded by sequence SEQ ID NO: 3. SEQ ID NO: 3 is the sequence encoding the second variable region of the antibodies secreted by cell line DSM ACC2987.

The first variable region according to SEQ ID NO: 6 may be encoded by sequence SEQ ID NO: 5 which is the sequence encoding the first variable region of the antibodies secreted by cell line DSM ACC2988. The second variable region according to SEQ ID NO: 8 may be encoded by sequence SEQ ID NO: 7. SEQ ID NO: 7 is the sequence encoding the second variable region of the antibodies secreted by cell line DSM ACC2988.

If the hybridoma cell line is DSM ACC2987, i.e., if the epitope is located on immunodominant *S. aureus* antigen IsaA, the epitope may comprise at least one amino acid sequence which is identical in at least 10, in particular in at least 11, in particular in at least 12, in particular in at least 13, in particular in at least 14, in particular in 15, amino acids with one of the sequences SEQ ID NO: 15, 17 to 19, 21 to 26, 32 to 34 and 57 according to the sequence listing.

Epitope mapping revealed that sequences SEQ ID NO: 15, 17 to 19, 21 to 26, 32 to 34 and 57 are involved in the binding of the antibodies or fragments to the epitope. The epitope may comprise more than one amino acid sequence as specified above. The epitope may even be formed by two or more sequences located apart from each other in the amino acid sequence of IsaA.

The antibodies or fragments according to the invention may be used as a medicament. Especially they may be used as a medicament for the treatment of a human being or an animal which human being or animal has an infection with *S. aureus*, especially methicillin resistant or methicillin sensitive *S. aureus*, or is at risk of getting such an infection. The human being or the animal may have a mastitis or a sepsis caused by the infection. The mastitis may be a bovine mastitis. If a cow has bovine mastitis no useable milk is produced by the cow and if the cow is treated with antibiotics as it is usual in this case the milk produced by this cow has to be discarded until no antibiotics are contained in the milk of this cow. This disadvantage of the usual treatment may be avoided by use of the antibodies or fragments according to the invention as a medicament for the treatment of the bovine mastitis.

The medicament may be a medicament that is prepared for systemic and/or local application. The inventors have recognized that the treatment of a severe *S. aureus* infection with the antibodies or fragments according to the invention results in a significant reduction of the mortality rates and number of *S. aureus* in the organs of the treated human being or animal. Furthermore, the inventors have recognized that phagocytotic killing of *S. aureus* bacteria by polymorphonuclear leukocytes is significantly enhanced if antibodies according to the invention are bound to *S. aureus* bacteria compared to *S. aureus* bacteria without these antibodies.

The antibodies or fragments may be present in a mixture with other antibodies or fragments of these other antibodies which other antibodies are directed against at least one further epitope of *Staphylococcus aureus*. This further epitope may be located on the antigen on which the epitope is located, i.e. IsaA or IsaB, or on a further antigen. The use of such a mixture as a medicament may be more efficient than the use of a medicament which solely contains the antibodies or fragments according to the invention. This may be owing to the high variability of *S. aureus* that causes different extents of expression of the antigens on different strains such that more bacteria are recognized by the mixture of antibodies or fragments than by the antibodies or fragments alone.

The antibodies or fragments may be present in a mixture with at least one antibiotic. In the human being or animal to be treated with the medicament mutated *S. aureus* may be present in addition to common *S. aureus*. The mutated *S. aureus* may have mutated IsaA and/or IsaB that cannot be recognized by the antibodies or fragments according to the invention. In this case the antibiotic may be effective against the mutated *S. aureus*.

The antibodies or fragments according to the invention may be present in a mixture with plasma of blood of a mammal, especially with plasma of blood of a human being. The inventors found, that antibodies or fragments according to the invention mixed with plasma may be much more efficient than antibodies or fragments according to the invention contained in a saline solution.

The invention also concerns a kit containing antibodies or fragments according to the invention for the detection of *S. aureus*. Such a kit may be used for diagnostic purposes.

The invention further concerns the use of antibodies or fragments according to the invention for the detection, especially a highly specific detection, of *S. aureus*.

Furthermore, the invention concerns a hybridoma cell line which produces antibodies according to the invention. The hybridoma cell line may be the cell line deposited at the DSMZ under accession number DSM ACC2987 or DSM ACC2988.

The invention further concerns a method of treatment of a human being or an animal which human being or animal has an infection with *Staphylococcus aureus*, especially methicillin resistant or methicillin sensitive *Staphylococcus aureus*, or is at risk of getting such an infection, wherein antibodies or fragments according to the invention are administered to the human being or the animal. The antibodies or fragments are administered in a dosage that is sufficient to reduce the amount of *S. aureus* or to cause an elimination of *S. aureus* in the human being or the animal. The antibodies or fragments may be mixed with a suitable carrier.

The human being or the animal may have a mastitis or a sepsis caused by the infection. The antibodies or fragments may be present in a mixture with other antibodies or fragments of these other antibodies which other antibodies are directed against at least one further epitope of *Staphylococcus aureus*. Furthermore, the antibodies or fragments may be mixed with plasma or blood of a mammal, especially a human being, before they are administered. The antibodies or fragments may be administered systemically, in particular intravenously, nasally or sublingually. They may also be administered together with at least one antibiotic.

EMBODIMENTS OF THE INVENTION

FIGS. 1a-1c show the result of stainings with monoclonal antibodies directed against epitopes of IsaA as primary antibodies that were produced by the hybridoma cell line DSM ACC2987 and that are designated as MAB-UK-66. FITC conjugated antibodies directed against mouse IgG were used as secondary antibodies.

Figure 1:
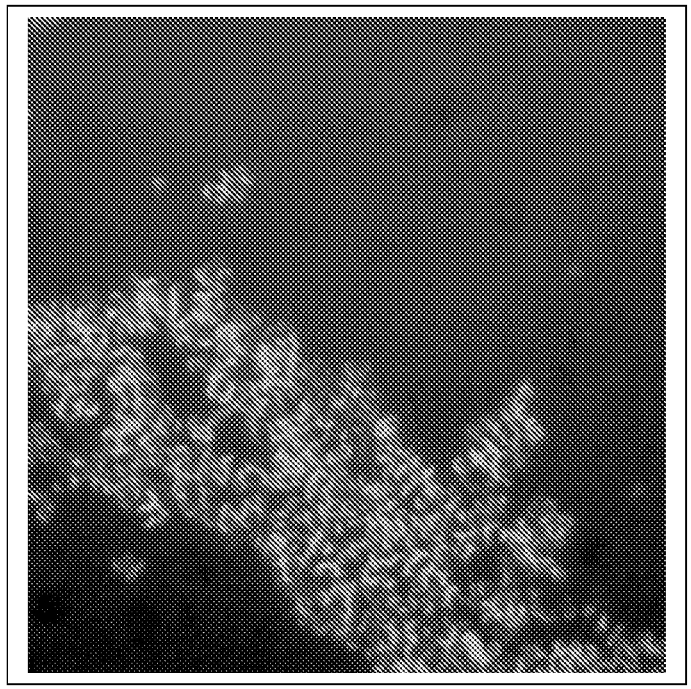
FIG. 1a, 1b, 1c show immunofluorescence stainings of *S. aureus* strain MA12 (FIG. 1a), *S. aureus* IsaA knock out strain MA12ΔisaA (FIG. 1b) and *S. aureus* protein A knock out strain Cowan I Δspa::Tc$^r$ (FIG. 1c) with antibodies according to the invention.
Figure 1:
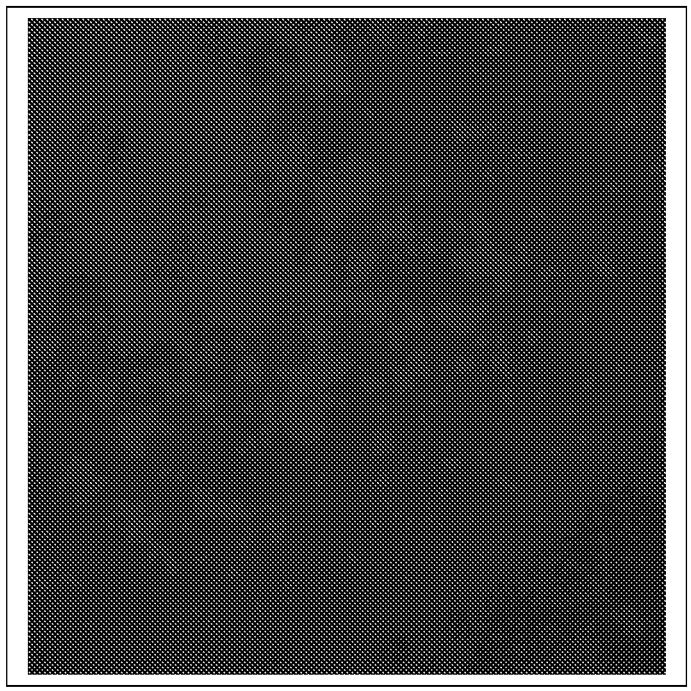
Figure 1C:
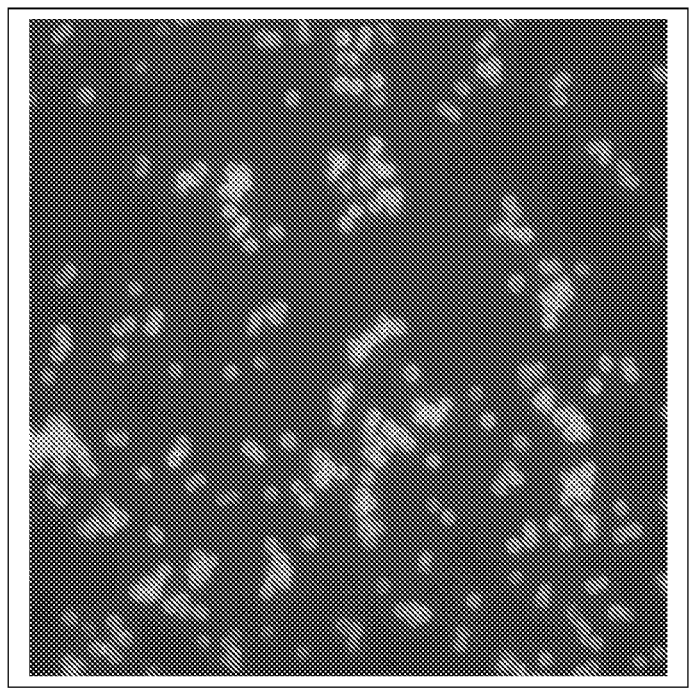

FIGS. 1a and 1c show positive immunofluorescence stainings of *S. aureus*, strains MA12 and Cowan I Δspa::Tc$^r$ whereas FIG. 1b shows no immunofluorescence staining of *S. aureus*, strain MA12ΔisaA. In contrast to native *S. aureus* bacteria the bacteria of *S. aureus* strain Cowan I Δspa::Tc$^r$ do not produce protein A. Protein A has a high affinity to the Fc-part of antibodies. The presence of protein A on the bacteria would result in a strong unspecific binding of the primary and secondary antibodies to the bacteria. Strain Cowan I Δspa::Tc$^r$ binds the primary antibodies indicating the presence of IsaA but no antibody cross reactivity with protein A.

Figure 2:
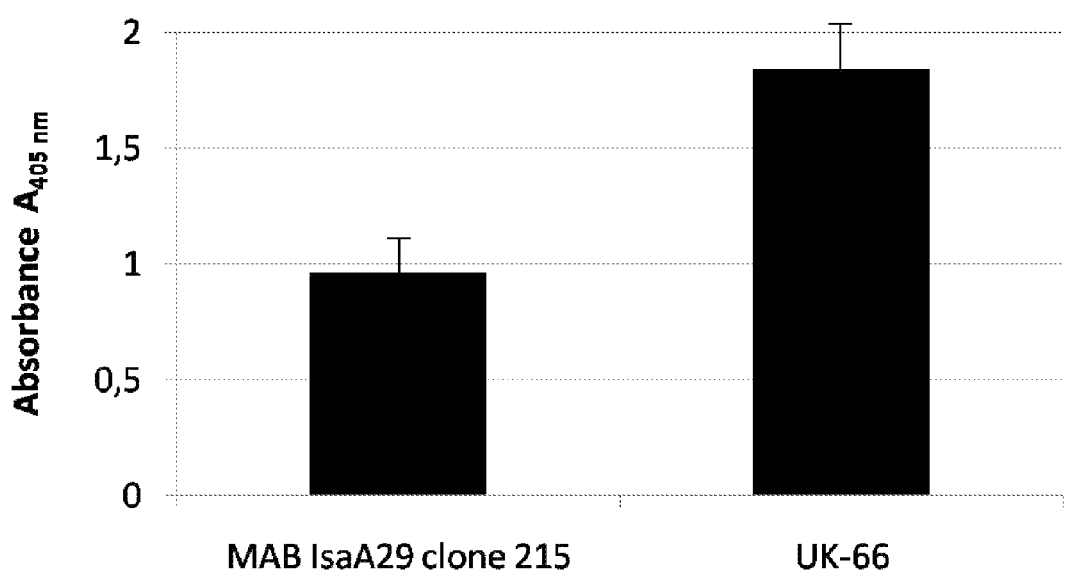
FIG. 2 shows ELISA data of IsaA binding of MAB-IsaA29 clone 215 compared to MAB-UK-66.

FIG. 2 shows the result of an Enzyme Linked Immuno Sorbent Assay (ELISA) that was performed to compare IsaA binding of known monoclonal antibody MAB-IsaA29 clone 215 with that of MAB-UK-66. MAB-IsaA29 clone 215 is the monoclonal antibody described in the abstracts "Development of antibody-based therapy targeting immunodominant antigens of *Staphylococcus aureus*", Ohlsen, K. et al., page 128 of the abstract book published for the 59$^{th}$ annual conference of the Deutsche Gesellschaft für Hygiene und Mikrobiologie e.V. on September 2007 and Lorenz, U. et al., "Therapeutische Effektivität von monoklonalen Antikörpern gegen *Staphylococcus aureus* in einem Sepsis- und Abszess-Mausmodell", Chirurgisches Forum 2008, Springer Berlin Heidelberg, 29$^{th}$ May 2008, issue 17, pp. 225-226. The ELISA was performed as follows:

After overnight coating of each well of a microtitre plate with a 100 µl sample of recombinant IsaA-protein (rIsaA) at a concentration of 0.5 µg/ml in phosphate-buffered saline (PBS, pH 7.4) the wells were blocked with 1% bovine serum albumin for 2 h. Above mentioned anti-IsaA antibodies were diluted in a ratio of 1 to 4,000 and added to the wells. After incubation for 1 h horseradish peroxidase-conjugated rabbit antimouse IgG (DAKO, Glostrup, Denmark) was added and incubated for 1 h. Then ABTS [2,2'-azinobis(3-ethylbenzthiazolinesulfonic acid)] substrate (Sigma Chemical Co., Deisenhofen, Germany) was added and incubated for 1 h. Absorbance was detected at 405 nm using a microplate autoreader. As can be seen from FIG. 1 the binding of MAB-UK-66 to rIsaA is much more intense than the binding of known antibody MAB-IsaA29 clone 215 to rIsaA.

Effective anti-*S. aureus* immunotherapy should protect mice against a lethal challenge of *S. aureus*. To investigate the efficiency of the antibodies according to the invention in vivo a survival model of *S. aureus* sepsis was established in mice as follows:

Age and gender matched NMRI mice (Charles River, Sulzfeld, Germany) were challenged on day 0 by intravenous injection with 5×10$^8$ colony forming units (cfu) of *S. aureus* USA300 (ATCC No. BAA-1556). Treated mice received intravenously MAB-UK-66 or isotype matched antibody as control (double dose regimen: 15 mg/kg in a volume of 100 µl PBS, pH 7.4 immediately and 24 h after bacterial challenge). Animals were monitored for 8 days, and lethal disease was recorded.

Figure 3:
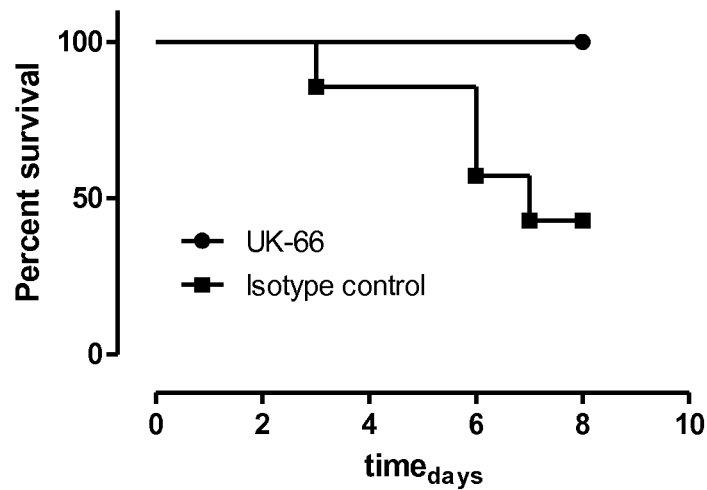
FIG. 3 shows survival of mice after i.v. challenge with *S. aureus* strain USA300 and i.v. treatment with monoclonal antibodies according to the invention or isotype control antibodies.

The significance of protection was measured with the Log-Rank/Mantel-Cox Test: P=0.022. The result is shown in FIG. 3.

For further investigation of the efficiency of the antibodies according to the invention in vivo a catheter related *S. aureus* sepsis model was established in mice as follows:

Age, gender and weight matched NMRI mice (Charles River Wiga Deutschland GmbH, 97633 Sulzfeld, Germany) were used in the experiment. Mice were intraperitoneally anesthetized with xylazin (8 mg/kg body weight)/ketamine (100 mg/kg body weight) and a minimal horizontal skin incision was made at the left side of the shaved neck. Using an operating microscope (Carl Zeiss Jena GmbH, 07745 Jena, Germany) under 10-16× magnification, the submaxillary gland was isolated to expose the bifurcation of anterior and posterior facial vein. A venotomy between loose ligatures on the isolated anterior facial vein was executed. A sterile single lumen polyethylene catheter (inner diameter 0.28 mm×outer diameter 0.6 mm) was inserted through the incision and advanced toward the superior vena cava. The ligatures were tied and the catheter was subcutaneously tunneled and exteriorized through midline scapular incision. The patency was tested, the catheter filled with heparin solution, sealed with a plug and left in place throughout the experiment. Twenty-four hours after surgery the mice were inoculated via the catheter with 100 µl of a *S. aureus* suspension, containing 1×10$^7$ cfu *S. aureus* bacteria, strain MA12. MA12 is a mucosal isolate from nursing staff described in Ohlsen, K., Ziebuhr, W., Koller, K. P., Hell, W., Wichelhaus, T. A., and Hacker, J. "Effects of subinhibitory concentrations of antibiotics on alpha-toxin (hla) gene expression of methicillin-sensitive and methicillin-resistant *Staphylococcus aureus* isolates", Antimicrob. Agents Chemother. (1998), 42, pages 2817 to 2823. The bacterial suspension was allowed to dwell within the catheter lumen for 15 minutes. The content of the catheter was then flushed in the mice with 0.2 ml 0.9% saline. Treated mice received the antibodies produced by the hybridoma cell line DSM ACC2987 i.v. (double dose regimen: 15 mg/kg in a volume of 100 μl immediately and 24 h after bacterial challenge) or saline i.v. (control group). Body weight and general appearance was assessed daily during the experiment. Five days post inoculation the mice were euthanized by $CO_2$ inhalation.

Figure 4:
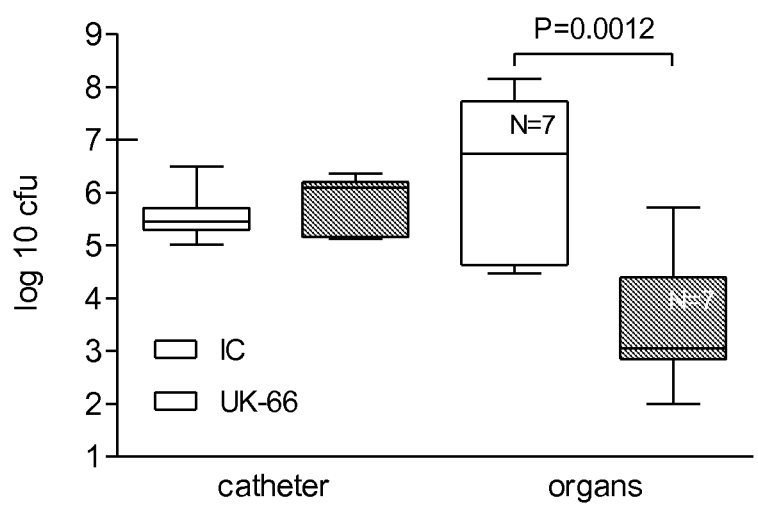
FIG. 4 shows the recovery of *S. aureus*, strain MA12 from a central venous catheter and organs of mice treated with *S. aureus* and monoclonal antibodies according to the invention.

Organs were aseptically harvested from euthanized mice and homogenized in 2 ml saline. Furthermore, the location of the catheter in the superior vena cava was confirmed and the explanted catheter irrigated with 2 ml saline and the irrigation fluid collected. Serial dilutions of the organ homogenates and catheter fluid collections were cultured on mannitol salt phenol red agar plates for at least 48 h at 37° C. Colony forming units were calculated as cfu/organ or cfu/catheter. The results are shown in FIG. 4. The data show that the treatment with the antibodies according to the invention resulted in a significant reduction of the bacterial load of the organs.

Figure 5:
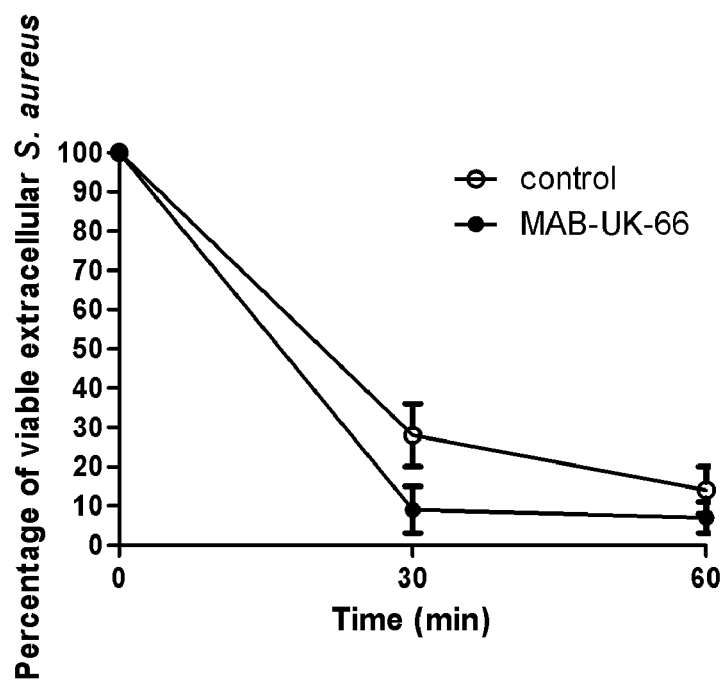
FIG. 5 shows the phagocytosis of *S. aureus* by polymorphonuclear leukocytes in presence and absence of antibodies according to the invention.

To investigate the effect of the antibodies according to the invention on phagocytosis human neutrophils were isolated using Polymorphprep (Nycomed, Oslo, Norway) in accordance with manufacturer's instructions. $1\times10^7$ cfu S. aureus MA12 in 1 ml Hanks' Balanced Salt Solution (HBSS) supplemented with 0.1% (wt/vol) gelatin (HBSS-gel) and 15% (vol/vol) purified MAB-UK-66 antibodies produced by the hybridoma cell line DSM ACC2987 or PBS (control) were incubated for 30 minutes at 37° C. in a slow shaking water bath. Equal volumes of $5\times10^6$ antibody- and PBS-treated S. aureus and $1\times10^6$ PMN-cells/ml HBSS-gel in a final volume of 1.5 ml were incubated at 37° C. under slow shaking. At intervals from zero to 60 minutes a sample of this suspension was removed, centrifuged for 4 minutes at 250×g, and the number of bacteria in the supernatant was determined by cfu counting. Phagocytosis is expressed as means of triplicate determinations±SD of the percentage number of extracellular bacteria. Statistical analysis was performed using the non-parametric Mann-Whitney U test. For all comparisons, a P value of <0.05 was considered statistically significant. Values were expressed as means±SD. The result shown in FIG. 5 demonstrates that S. aureus was phagocytized by polymorphonuclear leukocytes regardless of the presence of the antibodies according to the invention. However, with the antibodies according to the invention the phagocytosis process was significantly accelerated compared to the controls. The antibodies act as an opsonin for S. aureus phagocytosis by polymorphonuclear leukocytes.

To determine the affinity of the monoclonal antibodies MAB-UK-66 to IsaA the kinetics of the binding of these antibodies to immobilized IsaA was determined by means of measuring label-free surface plasmon resonance using the BIACORE®2000 system (GE Healthcare Europe GmbH, Munzinger Strasse 5, 79111 Freiburg, Germany). For the immobilization of the antigen IsaA was N-biotinylated by incubation with equimolar concentrations of sulfo-NHS-LC-biotin (Thermo Fisher Scientific, p/a Perbio Science, Adenauerallee 113, 53113 Bonn, Germany). Under these conditions the majority of the molecules was biotinylated only at a single site leaving the majority of the epitopes recognized by monoclonal antibodies MAB-UK-66 unaffected. Immobilization of the antigen to streptavidin coated matrices of biosensor CM5 chips was carried out as described in Nickel, J., Kotzsch, A., Sebald, W., and Mueller, T. D. "A single residue of GDF-5 defines binding specificity to BMP receptor IB" J. Mol. Biol. (2005), 349, pages 933 to 947. The amount of the immobilized antigen corresponds to about 100 resonance units [RU] measured by means of the BIACORE®2000 system.

Figure 6:
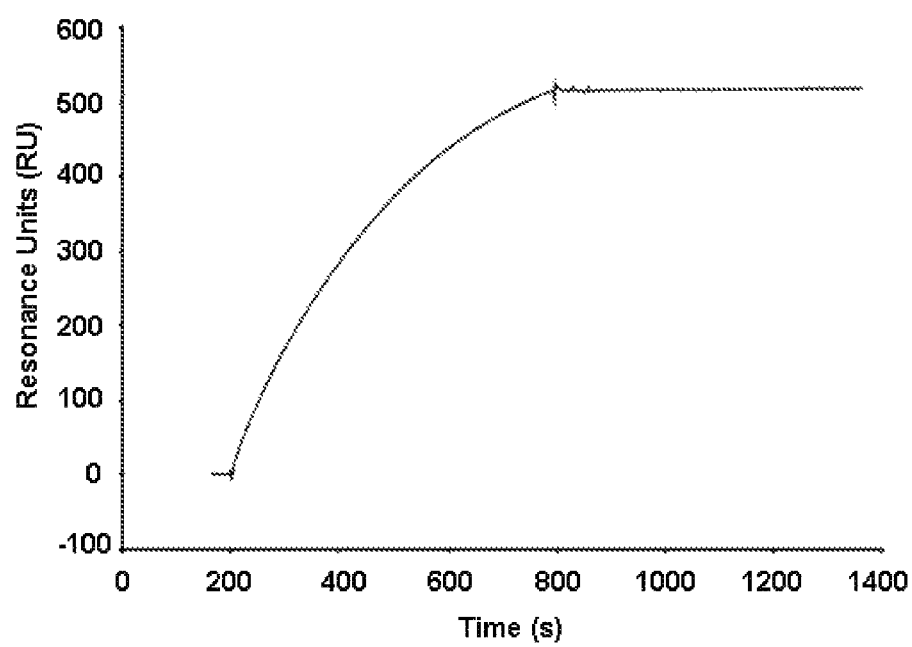
FIG. 6 shows the kinetics of the binding of monoclonal antibodies MAB-UK-66 to immobilized IsaA.

Interaction analyses were performed using HBS150 buffer (10 mM HEPES pH7.4, 150 mM NaCl, 3.4 mM EDTA). Sensorgrams were recorded at a flow rate of 10 pl/min at 25° C. The association and dissociation time was set to 10 min. The chips were regenerated after each cycle with different regeneration solutions (A: 1 mM $CH_3COOH$, 1 M NaCl, pH 3; B: 4 M $MgCl_2$; C: 1 mM $CH_3COOH$, 1 M NaCl, 6 M Urea, pH 3) for 2 min. The kinetics of the binding of these antibodies to immobilized IsaA is shown in FIG. 6.

All apparent binding affinities were calculated using the Biaevaluation software 2.2.4. Affinities of the interactions $k_{on}$ (<$10^6$ $M^{-1}s^{-1}$) and $k_{off}$ (<$10^{-2}$ $s^{-1}$) were calculated by fitting the kinetics data $k_{on}$ and $k_{off}$ to a 1:1 Langmuir binding model. In this way a dissociation constant $K_D$ was determined. The dissociation constant $K_D$ indicates the affinity between two interacting molecules (such as an antibody and the respective antigen). A low $K_D$ value indicates a high affinity whereas a high $K_D$ value indicates a low affinity. The standard deviation of $K_D$ values determined in this way is below 50%. Differences in binding affinities of more than a factor of two are therefore considered to be significant.

Under the measure conditions described above, the MAB-UK-66 antibodies interact with the 29 kDa IsaA antigens irreversibly due to not evaluatable slow off-rates. Since the evaluation of the kinetic rate constant is limited to $10^{-5}$ $sec^{-1}$ the observed off-rate has to be smaller than that value. By setting the off rate to $10^{-5}$ $sec^{-1}$ the on rate could be determined to be 5.6 $10^5$ $M^{-1}sec^{-1}$ resulting in a value for the dissociation constant of 1.8 $10^{-11}$ M. Therefore, the $K_D$ value for this interaction is ≤1.8 $10^{-11}$ M. Importantly, the antibody could not be removed after interaction with the antigen from the chip surface using all regeneration solutions described above. This indicates a very strong and highly specific interaction.

Figure 7:
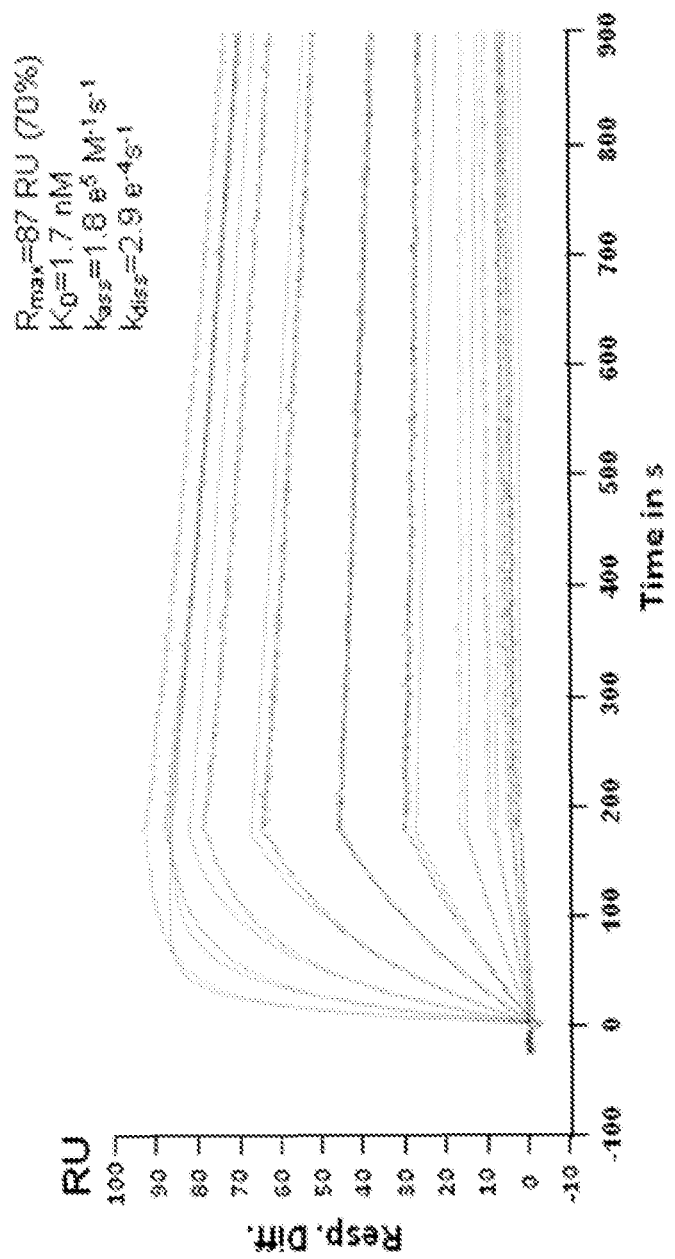
FIG. 7 shows the kinetics of the binding of IsaA to immobilized monoclonal antibodies MAB-UK-66.

To confirm the high affinity of the monoclonal antibody MAB-UK-66 to IsaA the kinetics of binding of IsaA to immobilized antibodies was determined by means of label-free surface plasmon resonance using the BIACORE®2000 system (GE Healthcare Europe GmbH, Munzinger Strasse 5, 79111 Freiburg, Germany). Reversible immobilization of the antibody MAB-UK-66 was performed using an anti mouse Fc antibody covalently coupled in high density (18700 resonance units RU) to a CM5 sensor surface according to manufacturer's instructions (Mouse Antibody Capture Kit, GE Healthcare). The average amount of captured antibody MAB-UK-66 onto the anti mouse Fc surface corresponds to about 640 RU. A blank anti mouse Fc surface was used as control surface for monitoring unspecific binding and performing reference subtraction. Interaction analyses were performed using HBS-EP buffer (10 mM HEPES pH 7.4, 150 mM NaCl, 3 mM EDTA, 0.005% Tween 20). Sensorgrams were recorded at a flow rate of 30 μl/min at 25° C. Association and dissociation times were set to 3 and 15 min, respectively. The anti-Fc capturing surfaces were regenerated after each cycle using short pulses of 10 mM glycine pH 1.7. The kinetics of the binding of IsaA to immobilized monoclonal antibodies MAB-UK-66 is shown in FIG. 7.

Affinities and rate constants for association ($k_{on}$) and for dissociation ($k_{off}$) were calculated using the BIAevaluation software 4.0.1 fitting the obtained sensorgrams to a 1:1 Langmuir binding model. In this way a dissociation constant $K_D$ of 1.7 nM was determined in two independent measurements. Rate constants for association and dissociation of the interaction between MAB-UK-66 and IsaA were determined to be 1.8 $10^5$ $M^{-1}s^{-1}$ ($k_{on}$) and 2.9 $10^{-4}$ $s^{-1}$ ($k_{off}$), respectively.

Under the measure conditions described above, the MAB-UK-66 antibody interacts with the 29 kDa IsaA antigen with a high affinity and slow off-rate confirming a strong and highly specific interaction as already determined by the binding of MAB-UK-66 antibodies to immobilized IsaA.

For characterizing the epitope of IsaA that is recognized by the antibodies or fragments according to the invention an epitope mapping was performed. For this oligopeptides of 15 amino acids in length have been synthesized. The sequence of each of the oligopeptides is identical with a sequence of 15 amino acids of IsaA. Each oligopeptide has an overlap of 11 amino acids with the oligopeptide representing a subsequent part of the total sequence. The sequences of the oligopeptides are sequences SEQ ID NO: 9 to 64 of the sequence listing.

Each oligopeptide was immobilized on a small spot on a glass side. Binding of the monoclonal antibodies secreted by the hybridoma cell line DSM ACC2987 and of control antibodies to these spots was examined upon incubation with these antibodies by binding of fluorescence labeled secondary antibodies and detecting fluorescence intensities. The results are shown in the following table:

| SEQ ID NO: | Binding of Antibodies Secreted by Cell Line DSM ACC2987 | Binding of Control Antibodies |
| --- | --- | --- |
| 9 | 273.3 | 70 |
| 10 | 227.7 | 159.7 |
| 11 | 101.3 | −11 |
| 12 | 679.7 | −22 |
| 13 | 5748 | 366.7 |
| 14 | 3190 | −35 |
| 15 | 11718.3 | 107 |
| 16 | 1951 | 117 |
| 17 | 17670.7 | 48 |
| 18 | 25327.7 | −118.7 |
| 19 | 31946.3 | 83.7 |
| 20 | 1053 | 105.7 |
| 21 | 33295 | 182.3 |
| 22 | 21481.7 | 26.3 |
| 23 | 63890.7 | 366.7 |
| 24 | 9359.3 | 79.3 |
| 25 | 49296 | −61.7 |
| 26 | 51825 | 261.3 |
| 27 | 441.7 | 81 |
| 28 | 3173.3 | 77.3 |
| 29 | 2486.3 | 85.7 |
| 30 | 1665.3 | −7 |
| 31 | 2935 | −20 |
| 32 | 59456 | 98.3 |
| 33 | 55515 | −0.7 |
| 34 | 29452.3 | 98.7 |
| 35 | 505.7 | 110.3 |
| 36 | 2745 | −14.3 |
| 37 | 139 | −27.3 |
| 38 | 975.3 | 97.7 |
| 39 | 491.3 | 109.3 |
| 40 | 6010 | −27 |
| 41 | 421 | 29.3 |
| 42 | 578.7 | 35.7 |
| 43 | 370.7 | 44.3 |
| 44 | 485.7 | 114.3 |
| 45 | 235 | −4.3 |
| 46 | 587 | −24.3 |
| 47 | 252 | 14.7 |
| 48 | 1168.3 | 397.7 |
| 49 | 399.3 | 40 |
| 50 | 192 | −49.7 |
| 51 | 139.3 | 58 |
| 52 | 284.7 | −60 |
| 53 | 577.3 | 70.3 |
| 54 | 569.7 | −51.7 |
| 55 | 1033.3 | 36 |
| 56 | 959 | −17.3 |
| 57 | 16756 | 312.7 |
| 58 | 1317.7 | 46.3 |
| 59 | 1404.3 | 132.3 |
| 60 | 3067.3 | 18.7 |
| 61 | 479 | 30.3 |
| 62 | 551.3 | 6.3 |
| 63 | 645.3 | 57.7 |
| 64 | 379 | 42 |

As can be seen from the above table sequences SEQ ID NO: 15, 17 to 19, 21 to 26, 32 to 34 and 57 are involved in the epitope binding of the antibodies secreted by cell line DSM ACC2987.

The invention claimed is:

1. An isolated antibody or fragment thereof, wherein said antibody or fragment thereof:
    (a) binds to an immunodominant *Staphylococcus aureus* antigen IsaA epitope and is secreted by the hybridoma cell line deposited at the DSMZ under accession number DSM ACC2987,
    (b) binds to an immunodominant *Staphylococcus aureus* antigen IsaA epitope selected from the group consisting of: SEQ ID NO: 15, 17-19, 21-26, 32-34 and 57,
    (c) binds to an immunodominant *Staphylococcus aureus* antigen IsaB epitope and is secreted by the hybridoma cell line deposited at the DSMZ under accession number DSM ACC2988, or
    (d) binds to an immunodominant *Staphylococcus aureus* antigen IsaB epitope and comprises a heavy chain variable region and a light chain variable region, wherein the sequence of the heavy chain variable region comprises SEQ ID NO:6 and the sequence of the light chain variable region comprises SEQ ID NO:8.

2. The isolated antibody or fragment thereof according to claim 1, wherein the antibody (b) or fragment thereof binds to the immunodominant *Staphylococcus aureus* antigen epitope to which the antibody secreted by the hybridoma cell line deposited at the DSMZ under accession number DSM ACC2987 binds, with a $K_D$ value of less than or equal to 1.7 nM.

3. The isolated antibody or fragment thereof according to claim 1(b) comprising a heavy chain variable region and a light chain variable region, and wherein the heavy chain variable region comprises SEQ ID NO:2, and the light chain variable region comprises SEQ ID NO: 4.

4. A hybridoma cell line which produces the antibody according to claim 1(a).

5. A hybridoma cell line which produces the antibody according to claim 1(c).

* * * * *

SEQUENCE LISTING

<160> NUMBER OF SEQ ID NOS: 64

<210> SEQ ID NO 1
<211> LENGTH: 360
<212> TYPE: DNA
<213> ORGANISM: Mus musculus

<400> SEQUENCE: 1

```
atggccgatg tcaagcttgt ggaatctggg ggaggcttag tgaagcttgg agggtccctg      60
aaactctcct gttcagcctc tggattcact ttcagtaact attacatgtc ttgggttcgc     120
cagactccag agaagaggct ggagttggtc gcagacatta atggtaatgg tggtagcacc     180
tactatccag acactgtgaa gggccgattc accatctcca gagacaatgc caagaacacc     240
ctgtacctgc aaatgagcag tctgaagtct gaggacacag ccttgtatta ctgtgtaaga     300
cgggggggtt actacgccct tgactactgg ggccaaggga ccacggtcac cgtctcgagt     360
```

<210> SEQ ID NO 2
<211> LENGTH: 120
<212> TYPE: PRT
<213> ORGANISM: Mus musculus

<400> SEQUENCE: 2

Met Ala Asp Val Lys Leu Val Glu Ser Gly Gly Gly Leu Val Lys Leu
1               5                   10                  15

Gly Gly Ser Leu Lys Leu Ser Cys Ser Ala Ser Gly Phe Thr Phe Ser
            20                  25                  30

Asn Tyr Tyr Met Ser Trp Val Arg Gln Thr Pro Glu Lys Arg Leu Glu
            35                  40                  45

Leu Val Ala Asp Ile Asn Gly Asn Gly Gly Ser Thr Tyr Tyr Pro Asp
    50                  55                  60

Thr Val Lys Gly Arg Phe Thr Ile Ser Arg Asp Asn Ala Lys Asn Thr
65                  70                  75                  80

Leu Tyr Leu Gln Met Ser Ser Leu Lys Ser Glu Asp Thr Ala Leu Tyr
                85                  90                  95

Tyr Cys Val Arg Arg Gly Gly Tyr Tyr Ala Leu Asp Tyr Trp Gly Gln
            100                 105                 110

Gly Thr Thr Val Thr Val Ser Ser
            115                 120

<210> SEQ ID NO 3
<211> LENGTH: 340
<212> TYPE: DNA
<213> ORGANISM: Mus musculus

<400> SEQUENCE: 3
gatgtggtga tgacccagac cccgctctcc ctgcctgtca gtcttggaga tcaagcctcc      60
atctcttgca gatctagtca gagccttgtg cacattaatg gaaacaccta tttacattgg    120
tacctgcaga agccaggcca gtctccaaag ctcctgatct acagagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttccg    300
tggacgttcg gtggagggac caagctggag ctgaaacggg                          340

<210> SEQ ID NO 4
<211> LENGTH: 113
<212> TYPE: PRT
<213> ORGANISM: Mus musculus

<400> SEQUENCE: 4

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ile
            20                  25                  30

Asn Gly Asn Thr Tyr Leu His Trp Tyr Leu Gln Lys Pro Gly Gln Ser
            35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Leu Lys
            100                 105                 110

Arg

<210> SEQ ID NO 5

-continued

```
<211> LENGTH: 354
<212> TYPE: DNA
<213> ORGANISM: Mus musculus

<400> SEQUENCE: 5
gaggtgcaac tgcagcagtc tgggactgtg ctggcaaggc ctggggcttc agtgaagatg      60
tcctgcaagg cttctggcta cacctttacc acctactgga tgcactgggt aaaacagagg     120
cctggacagg gtctggaatg gattggcgct atttatcctg gaatagtgat aaaatgttca     180
aaccagaagt tcaaggacag ggccaaactg attgcagtca cgtccaccag cactgcctac     240
atggagctca gcagcctgac aaatgaggac tctgcggtct attactgtac aagaggaact     300
gggacggaaa tttggtttgc ttactggggc caagggacca cggtcaccgt ctcg           354

<210> SEQ ID NO 6
<211> LENGTH: 118
<212> TYPE: PRT
<213> ORGANISM: Mus musculus
<220> FEATURE:
<221> NAME/KEY: MISC_FEATURE
<222> LOCATION: (58)..(60)
<223> OTHER INFORMATION: Xaa Xaa Xaa can be Lys Met Phe or Thr Ser Tyr
      or Thr Thr Tyr
<220> FEATURE:
<221> NAME/KEY: MISC_FEATURE
<222> LOCATION: (66)..(66)
<223> OTHER INFORMATION: Xaa can be Asp or Gly
<220> FEATURE:
<221> NAME/KEY: MISC_FEATURE
<222> LOCATION: (67)..(67)
<223> OTHER INFORMATION: Xaa can be Arg or Lys

<400> SEQUENCE: 6

Glu Val Gln Leu Gln Gln Ser Gly Thr Val Leu Ala Arg Pro Gly Ala
1               5                  10                  15

Ser Val Lys Met Ser Cys Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Ser Asp Xaa Xaa Xaa Asn Gln Lys Phe
    50                  55                  60

Lys Xaa Xaa Ala Lys Leu Ile Ala Val Thr Ser Thr Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Gly Thr Gly Thr Glu Ile Trp Phe Ala Tyr Trp Gly Gln Gly
            100                 105                 110

Thr Thr Val Thr Val Ser
        115

<210> SEQ ID NO 7
<211> LENGTH: 338
<212> TYPE: DNA
<213> ORGANISM: Mus musculus

<400> SEQUENCE: 7
agtgcacaga ttttgctgac ccaatctcca tcctccttat ctgcctctct gggagaaaga      60
gtcagtctca cttgtagggc aagtcaggac attggtacta gcttaaactg gcttcagagg     120
gaaccagatg gaactattaa acgcctgatc tacgccacat ccagtttaga ttctggtgtc     180
cccaaaaggt tcagtggcag taggtctggg tcagattatt ctctcaccat cagcagcctt     240
gagtctgaag attttgtaga ctattactgt gtccaatatg tcagttctcc attcacgttc     300
```

```
ggctcgggga ccaagctgga gctgaaacgg gcggccgc                                338
```

<210> SEQ ID NO 8
<211> LENGTH: 112
<212> TYPE: PRT
<213> ORGANISM: Mus musculus
<220> FEATURE:
<221> NAME/KEY: MISC_FEATURE
<222> LOCATION: (5)..(6)
<223> OTHER INFORMATION: Xaa Xaa can be Leu Leu or Gln Met
<220> FEATURE:
<221> NAME/KEY: MISC_FEATURE
<222> LOCATION: (33)..(33)
<223> OTHER INFORMATION: Xaa can be Thr or Ser
<220> FEATURE:
<221> NAME/KEY: MISC_FEATURE
<222> LOCATION: (40)..(40)
<223> OTHER INFORMATION: Xaa can be Arg or Gln
<220> FEATURE:
<221> NAME/KEY: MISC_FEATURE
<222> LOCATION: (91)..(91)
<223> OTHER INFORMATION: Xaa can be Val or Leu
<220> FEATURE:
<221> NAME/KEY: MISC_FEATURE
<222> LOCATION: (94)..(94)
<223> OTHER INFORMATION: Xaa can be Val or Ala
<220> FEATURE:
<221> NAME/KEY: MISC_FEATURE
<222> LOCATION: (108)..(108)
<223> OTHER INFORMATION: Xaa can be Leu or Ile

<400> SEQUENCE: 8

Ser Ala Gln Ile Xaa Xaa Thr Gln Ser Pro Ser Ser Leu Ser Ala Ser
1               5                   10                  15

Leu Gly Glu Arg Val Ser Leu Thr Cys Arg Ala Ser Gln Asp Ile Gly
            20                  25                  30

Xaa Ser Leu Asn Trp Leu Gln Xaa Glu Pro Asp Gly Thr Ile Lys Arg
        35                  40                  45

Leu Ile Tyr Ala Thr Ser Ser Leu Asp Ser Gly Val Pro Lys Arg Phe
    50                  55                  60

Ser Gly Ser Arg Ser Gly Ser Asp Tyr Ser Leu Thr Ile Ser Ser Leu
65                  70                  75                  80

Glu Ser Glu Asp Phe Val Asp Tyr Tyr Cys Xaa Gln Tyr Xaa Ser Ser
                85                  90                  95

Pro Phe Thr Phe Gly Ser Gly Thr Lys Leu Glu Xaa Lys Arg Ala Ala
            100                 105                 110

<210> SEQ ID NO 9
<211> LENGTH: 15
<212> TYPE: PRT
<213> ORGANISM: Staphylococcus aureus

<400> SEQUENCE: 9

Met Lys Lys Thr Ile Met Ala Ser Ser Leu Ala Val Ala Leu Gly
1               5                   10                  15

<210> SEQ ID NO 10
<211> LENGTH: 15
<212> TYPE: PRT
<213> ORGANISM: Staphylococcus aureus

<400> SEQUENCE: 10

Ile Met Ala Ser Ser Leu Ala Val Ala Leu Gly Val Thr Gly Tyr
1               5                   10                  15

<210> SEQ ID NO 11

```
<211> LENGTH: 15
<212> TYPE: PRT
<213> ORGANISM: Staphylococcus aureus

<400> SEQUENCE: 11

Ser Leu Ala Val Ala Leu Gly Val Thr Gly Tyr Ala Ala Gly Thr
1               5                   10                  15

<210> SEQ ID NO 12
<211> LENGTH: 15
<212> TYPE: PRT
<213> ORGANISM: Staphylococcus aureus

<400> SEQUENCE: 12

Ala Leu Gly Val Thr Gly Tyr Ala Ala Gly Thr Gly His Gln Ala
1               5                   10                  15

<210> SEQ ID NO 13
<211> LENGTH: 15
<212> TYPE: PRT
<213> ORGANISM: Staphylococcus aureus

<400> SEQUENCE: 13

Thr Gly Tyr Ala Ala Gly Thr Gly His Gln Ala His Ala Ala Glu
1               5                   10                  15

<210> SEQ ID NO 14
<211> LENGTH: 15
<212> TYPE: PRT
<213> ORGANISM: Staphylococcus aureus

<400> SEQUENCE: 14

Ala Gly Thr Gly His Gln Ala His Ala Ala Glu Val Asn Val Asp
1               5                   10                  15

<210> SEQ ID NO 15
<211> LENGTH: 15
<212> TYPE: PRT
<213> ORGANISM: Staphylococcus aureus

<400> SEQUENCE: 15

His Gln Ala His Ala Ala Glu Val Asn Val Asp Gln Ala His Leu
1               5                   10                  15

<210> SEQ ID NO 16
<211> LENGTH: 15
<212> TYPE: PRT
<213> ORGANISM: Staphylococcus aureus

<400> SEQUENCE: 16

Ala Ala Glu Val Asn Val Asp Gln Ala His Leu Val Asp Leu Ala
1               5                   10                  15

<210> SEQ ID NO 17
<211> LENGTH: 15
<212> TYPE: PRT
<213> ORGANISM: Staphylococcus aureus

<400> SEQUENCE: 17

Asn Val Asp Gln Ala His Leu Val Asp Leu Ala His Asn His Gln
1               5                   10                  15

<210> SEQ ID NO 18
<211> LENGTH: 15
<212> TYPE: PRT
<213> ORGANISM: Staphylococcus aureus
```

-continued

<400> SEQUENCE: 18

Ala His Leu Val Asp Leu Ala His Asn His Gln Asp Gln Leu Asn
1               5                   10                  15

<210> SEQ ID NO 19
<211> LENGTH: 15
<212> TYPE: PRT
<213> ORGANISM: Staphylococcus aureus

<400> SEQUENCE: 19

Asp Leu Ala His Asn His Gln Asp Gln Leu Asn Ala Ala Pro Ile
1               5                   10                  15

<210> SEQ ID NO 20
<211> LENGTH: 15
<212> TYPE: PRT
<213> ORGANISM: Staphylococcus aureus

<400> SEQUENCE: 20

Asn His Gln Asp Gln Leu Asn Ala Ala Pro Ile Lys Asp Gly Ala
1               5                   10                  15

<210> SEQ ID NO 21
<211> LENGTH: 15
<212> TYPE: PRT
<213> ORGANISM: Staphylococcus aureus

<400> SEQUENCE: 21

Gln Leu Asn Ala Ala Pro Ile Lys Asp Gly Ala Tyr Asp Ile His
1               5                   10                  15

<210> SEQ ID NO 22
<211> LENGTH: 15
<212> TYPE: PRT
<213> ORGANISM: Staphylococcus aureus

<400> SEQUENCE: 22

Ala Pro Ile Lys Asp Gly Ala Tyr Asp Ile His Phe Val Lys Asp
1               5                   10                  15

<210> SEQ ID NO 23
<211> LENGTH: 15
<212> TYPE: PRT
<213> ORGANISM: Staphylococcus aureus

<400> SEQUENCE: 23

Asp Gly Ala Tyr Asp Ile His Phe Val Lys Asp Gly Phe Gln Tyr
1               5                   10                  15

<210> SEQ ID NO 24
<211> LENGTH: 15
<212> TYPE: PRT
<213> ORGANISM: Staphylococcus aureus

<400> SEQUENCE: 24

Asp Ile His Phe Val Lys Asp Gly Phe Gln Tyr Asn Phe Thr Ser
1               5                   10                  15

<210> SEQ ID NO 25
<211> LENGTH: 15
<212> TYPE: PRT
<213> ORGANISM: Staphylococcus aureus

<400> SEQUENCE: 25

Val Lys Asp Gly Phe Gln Tyr Asn Phe Thr Ser Asn Gly Thr Thr
1               5                   10                  15

<210> SEQ ID NO 26
<211> LENGTH: 15
<212> TYPE: PRT
<213> ORGANISM: Staphylococcus aureus

<400> SEQUENCE: 26

Phe Gln Tyr Asn Phe Thr Ser Asn Gly Thr Thr Trp Ser Trp Ser
1               5                   10                  15

<210> SEQ ID NO 27
<211> LENGTH: 15
<212> TYPE: PRT
<213> ORGANISM: Staphylococcus aureus

<400> SEQUENCE: 27

Phe Thr Ser Asn Gly Thr Thr Trp Ser Trp Ser Tyr Glu Ala Ala
1               5                   10                  15

<210> SEQ ID NO 28
<211> LENGTH: 15
<212> TYPE: PRT
<213> ORGANISM: Staphylococcus aureus

<400> SEQUENCE: 28

Gly Thr Thr Trp Ser Trp Ser Tyr Glu Ala Ala Asn Gly Gln Thr
1               5                   10                  15

<210> SEQ ID NO 29
<211> LENGTH: 15
<212> TYPE: PRT
<213> ORGANISM: Staphylococcus aureus

<400> SEQUENCE: 29

Ser Trp Ser Tyr Glu Ala Ala Asn Gly Gln Thr Ala Gly Phe Ser
1               5                   10                  15

<210> SEQ ID NO 30
<211> LENGTH: 15
<212> TYPE: PRT
<213> ORGANISM: Staphylococcus aureus

<400> SEQUENCE: 30

Glu Ala Ala Asn Gly Gln Thr Ala Gly Phe Ser Asn Val Ala Gly
1               5                   10                  15

<210> SEQ ID NO 31
<211> LENGTH: 15
<212> TYPE: PRT
<213> ORGANISM: Staphylococcus aureus

<400> SEQUENCE: 31

Gly Gln Thr Ala Gly Phe Ser Asn Val Ala Gly Ala Asp Tyr Thr
1               5                   10                  15

<210> SEQ ID NO 32
<211> LENGTH: 15
<212> TYPE: PRT
<213> ORGANISM: Staphylococcus aureus

<400> SEQUENCE: 32

Gly Phe Ser Asn Val Ala Gly Ala Asp Tyr Thr Thr Ser Tyr Asn
1               5                   10                  15

```
<210> SEQ ID NO 33
<211> LENGTH: 15
<212> TYPE: PRT
<213> ORGANISM: Staphylococcus aureus

<400> SEQUENCE: 33

Val Ala Gly Ala Asp Tyr Thr Thr Ser Tyr Asn Gln Gly Ser Asp
1               5                   10                  15

<210> SEQ ID NO 34
<211> LENGTH: 15
<212> TYPE: PRT
<213> ORGANISM: Staphylococcus aureus

<400> SEQUENCE: 34

Asp Tyr Thr Thr Ser Tyr Asn Gln Gly Ser Asp Val Gln Ser Val
1               5                   10                  15

<210> SEQ ID NO 35
<211> LENGTH: 15
<212> TYPE: PRT
<213> ORGANISM: Staphylococcus aureus

<400> SEQUENCE: 35

Ser Tyr Asn Gln Gly Ser Asp Val Gln Ser Val Ser Tyr Asn Ala
1               5                   10                  15

<210> SEQ ID NO 36
<211> LENGTH: 15
<212> TYPE: PRT
<213> ORGANISM: Staphylococcus aureus

<400> SEQUENCE: 36

Gly Ser Asp Val Gln Ser Val Ser Tyr Asn Ala Gln Ser Ser Asn
1               5                   10                  15

<210> SEQ ID NO 37
<211> LENGTH: 15
<212> TYPE: PRT
<213> ORGANISM: Staphylococcus aureus

<400> SEQUENCE: 37

Gln Ser Val Ser Tyr Asn Ala Gln Ser Ser Asn Ser Asn Val Glu
1               5                   10                  15

<210> SEQ ID NO 38
<211> LENGTH: 15
<212> TYPE: PRT
<213> ORGANISM: Staphylococcus aureus

<400> SEQUENCE: 38

Tyr Asn Ala Gln Ser Ser Asn Ser Asn Val Glu Ala Val Ser Ala
1               5                   10                  15

<210> SEQ ID NO 39
<211> LENGTH: 15
<212> TYPE: PRT
<213> ORGANISM: Staphylococcus aureus

<400> SEQUENCE: 39

Ser Ser Asn Ser Asn Val Glu Ala Val Ser Ala Pro Thr Tyr His
1               5                   10                  15

<210> SEQ ID NO 40
<211> LENGTH: 15
```

```
<212> TYPE: PRT
<213> ORGANISM: Staphylococcus aureus

<400> SEQUENCE: 40

Asn Val Glu Ala Val Ser Ala Pro Thr Tyr His Asn Tyr Ser Thr
1               5                   10                  15

<210> SEQ ID NO 41
<211> LENGTH: 15
<212> TYPE: PRT
<213> ORGANISM: Staphylococcus aureus

<400> SEQUENCE: 41

Val Ser Ala Pro Thr Tyr His Asn Tyr Ser Thr Ser Thr Thr Ser
1               5                   10                  15

<210> SEQ ID NO 42
<211> LENGTH: 15
<212> TYPE: PRT
<213> ORGANISM: Staphylococcus aureus

<400> SEQUENCE: 42

Thr Tyr His Asn Tyr Ser Thr Ser Thr Thr Ser Ser Ser Val Arg
1               5                   10                  15

<210> SEQ ID NO 43
<211> LENGTH: 15
<212> TYPE: PRT
<213> ORGANISM: Staphylococcus aureus

<400> SEQUENCE: 43

Tyr Ser Thr Ser Thr Thr Ser Ser Ser Val Arg Leu Ser Asn Gly
1               5                   10                  15

<210> SEQ ID NO 44
<211> LENGTH: 15
<212> TYPE: PRT
<213> ORGANISM: Staphylococcus aureus

<400> SEQUENCE: 44

Thr Thr Ser Ser Ser Val Arg Leu Ser Asn Gly Asn Thr Ala Gly
1               5                   10                  15

<210> SEQ ID NO 45
<211> LENGTH: 15
<212> TYPE: PRT
<213> ORGANISM: Staphylococcus aureus

<400> SEQUENCE: 45

Ser Val Arg Leu Ser Asn Gly Asn Thr Ala Gly Ala Thr Gly Ser
1               5                   10                  15

<210> SEQ ID NO 46
<211> LENGTH: 15
<212> TYPE: PRT
<213> ORGANISM: Staphylococcus aureus

<400> SEQUENCE: 46

Ser Asn Gly Asn Thr Ala Gly Ala Thr Gly Ser Ser Ala Ala Gln
1               5                   10                  15

<210> SEQ ID NO 47
<211> LENGTH: 15
<212> TYPE: PRT
<213> ORGANISM: Staphylococcus aureus
```

```
<400> SEQUENCE: 47

Thr Ala Gly Ala Thr Gly Ser Ser Ala Ala Gln Ile Met Ala Gln
1               5                   10                  15

<210> SEQ ID NO 48
<211> LENGTH: 15
<212> TYPE: PRT
<213> ORGANISM: Staphylococcus aureus

<400> SEQUENCE: 48

Thr Gly Ser Ser Ala Ala Gln Ile Met Ala Gln Arg Thr Gly Val
1               5                   10                  15

<210> SEQ ID NO 49
<211> LENGTH: 15
<212> TYPE: PRT
<213> ORGANISM: Staphylococcus aureus

<400> SEQUENCE: 49

Ala Ala Gln Ile Met Ala Gln Arg Thr Gly Val Ser Ala Ser Thr
1               5                   10                  15

<210> SEQ ID NO 50
<211> LENGTH: 15
<212> TYPE: PRT
<213> ORGANISM: Staphylococcus aureus

<400> SEQUENCE: 50

Met Ala Gln Arg Thr Gly Val Ser Ala Ser Thr Trp Ala Ala Ile
1               5                   10                  15

<210> SEQ ID NO 51
<211> LENGTH: 15
<212> TYPE: PRT
<213> ORGANISM: Staphylococcus aureus

<400> SEQUENCE: 51

Thr Gly Val Ser Ala Ser Thr Trp Ala Ala Ile Ile Ala Arg Glu
1               5                   10                  15

<210> SEQ ID NO 52
<211> LENGTH: 15
<212> TYPE: PRT
<213> ORGANISM: Staphylococcus aureus

<400> SEQUENCE: 52

Ala Ser Thr Trp Ala Ala Ile Ile Ala Arg Glu Ser Asn Gly Gln
1               5                   10                  15

<210> SEQ ID NO 53
<211> LENGTH: 15
<212> TYPE: PRT
<213> ORGANISM: Staphylococcus aureus

<400> SEQUENCE: 53

Ala Ala Ile Ile Ala Arg Glu Ser Asn Gly Gln Val Asn Ala Tyr
1               5                   10                  15

<210> SEQ ID NO 54
<211> LENGTH: 15
<212> TYPE: PRT
<213> ORGANISM: Staphylococcus aureus

<400> SEQUENCE: 54

Ala Arg Glu Ser Asn Gly Gln Val Asn Ala Tyr Asn Pro Ser Gly
```

<210> SEQ ID NO 55
<211> LENGTH: 15
<212> TYPE: PRT
<213> ORGANISM: Staphylococcus aureus

<400> SEQUENCE: 55

Asn Gly Gln Val Asn Ala Tyr Asn Pro Ser Gly Ala Ser Gly Leu
1               5                   10                  15

<210> SEQ ID NO 56
<211> LENGTH: 15
<212> TYPE: PRT
<213> ORGANISM: Staphylococcus aureus

<400> SEQUENCE: 56

Asn Ala Tyr Asn Pro Ser Gly Ala Ser Gly Leu Phe Gln Thr Met
1               5                   10                  15

<210> SEQ ID NO 57
<211> LENGTH: 15
<212> TYPE: PRT
<213> ORGANISM: Staphylococcus aureus

<400> SEQUENCE: 57

Pro Ser Gly Ala Ser Gly Leu Phe Gln Thr Met Pro Gly Trp Gly
1               5                   10                  15

<210> SEQ ID NO 58
<211> LENGTH: 15
<212> TYPE: PRT
<213> ORGANISM: Staphylococcus aureus

<400> SEQUENCE: 58

Ser Gly Leu Phe Gln Thr Met Pro Gly Trp Gly Pro Thr Asn Thr
1               5                   10                  15

<210> SEQ ID NO 59
<211> LENGTH: 15
<212> TYPE: PRT
<213> ORGANISM: Staphylococcus aureus

<400> SEQUENCE: 59

Gln Thr Met Pro Gly Trp Gly Pro Thr Asn Thr Val Asp Gln Gln
1               5                   10                  15

<210> SEQ ID NO 60
<211> LENGTH: 15
<212> TYPE: PRT
<213> ORGANISM: Staphylococcus aureus

<400> SEQUENCE: 60

Gly Trp Gly Pro Thr Asn Thr Val Asp Gln Gln Ile Asn Ala Ala
1               5                   10                  15

<210> SEQ ID NO 61
<211> LENGTH: 15
<212> TYPE: PRT
<213> ORGANISM: Staphylococcus aureus

<400> SEQUENCE: 61

Thr Asn Thr Val Asp Gln Gln Ile Asn Ala Ala Val Lys Ala Tyr
1               5                   10                  15

-continued

```
<210> SEQ ID NO 62
<211> LENGTH: 15
<212> TYPE: PRT
<213> ORGANISM: Staphylococcus aureus

<400> SEQUENCE: 62

Asp Gln Gln Ile Asn Ala Ala Val Lys Ala Tyr Lys Ala Gln Gly
1               5                   10                  15

<210> SEQ ID NO 63
<211> LENGTH: 15
<212> TYPE: PRT
<213> ORGANISM: Staphylococcus aureus

<400> SEQUENCE: 63

Asn Ala Ala Val Lys Ala Tyr Lys Ala Gln Gly Leu Gly Ala Trp
1               5                   10                  15

<210> SEQ ID NO 64
<211> LENGTH: 15
<212> TYPE: PRT
<213> ORGANISM: Staphylococcus aureus

<400> SEQUENCE: 64

Ala Val Lys Ala Tyr Lys Ala Gln Gly Leu Gly Ala Trp Gly Phe
1               5                   10                  15
```